United States Patent
Tang et al.

(10) Patent No.: US 9,629,923 B2
(45) Date of Patent: Apr. 25, 2017

(54) CISPLATIN COMPLEX AND PREPARATION METHOD THEREOF

(71) Applicant: CHANGCHUN INSTITUTE OF APPLIED CHEMISTRY, CHINESE ACADEMY OF SCIENCE, Changchun, Jilin (CN)

(72) Inventors: Zhaohui Tang, Changchun (CN); Haiyang Yu, Changchun (CN); Wantong Song, Changchun (CN); Mingqiang Li, Changchun (CN); Xiuli Zuang, Changchun (CN); Xuesi Chen, Changchun (CN)

(73) Assignee: Changchun Institute of Applied Chemistry, Chinese Academy of Science, Jilin (CN)

( * ) Notice: Subject to any disclaimer, the term of this patent is extended or adjusted under 35 U.S.C. 154(b) by 109 days.

(21) Appl. No.: 14/434,731

(22) PCT Filed: Mar. 26, 2013

(86) PCT No.: PCT/CN2013/073165
§ 371 (c)(1),
(2) Date: Apr. 9, 2015

(87) PCT Pub. No.: WO2014/056304
PCT Pub. Date: Apr. 17, 2014

(65) Prior Publication Data
US 2015/0231273 A1    Aug. 20, 2015

(30) Foreign Application Priority Data
Oct. 10, 2012  (CN) .......................... 2012 1 0382696

(51) Int. Cl.
*C08G 69/48* (2006.01)
*C08G 81/00* (2006.01)
*A61K 47/48* (2006.01)
*A61K 33/24* (2006.01)

(52) U.S. Cl.
CPC ........ *A61K 47/48246* (2013.01); *A61K 33/24* (2013.01); *A61K 47/48215* (2013.01); *C08G 81/00* (2013.01)

(58) Field of Classification Search
None
See application file for complete search history.

(56) References Cited

U.S. PATENT DOCUMENTS 5,871,710 A * 2/1999 Bogdanov ........ A61K 47/48169
424/1.65

FOREIGN PATENT DOCUMENTS

| CN | 101455843 A | 6/2009 |
|----|----|----|
| CN | 102093554 A | 6/2011 |
| CN | 102604082 B | 7/2012 |
| CN | 102863627 B | 1/2013 |
| WO | 2007/116965 A1 | 10/2007 |

OTHER PUBLICATIONS

International Search Report dated Jul. 4, 2013 for PCT/CN2013/073165.

* cited by examiner

*Primary Examiner* — Ana Woodward
(74) *Attorney, Agent, or Firm* — Knobbe, Martens, Olson & Bear, LLP

(57) ABSTRACT

A CDDP complex is formed by complexation of CDDP and a polymer having a structure of Formula (I). The CDDP complex has good biocompatibility and is degradable. A side chain of the polymer is grafted with polyethylene glycol, which gives the CDDP complex good dissolvability. When dissolved in an aqueous medium, the CDDP is protected by a hydrophilic polyethylene glycol chain segment and a hydrophobic amino acid chain segment, which can effectively avoid a sudden release of the CDDP due to the influence of the blood circulation system after intravenous injection, thus improving the stability of the CDDP complex. A carboxyl group contained in the CDDP complex has pH value sensitivity and tends to be deprotonated in a low pH environment, which is advantageous for promoting the release of a drug, and improving the efficiency of the drug.

10 Claims, 5 Drawing Sheets

CISPLATIN COMPLEX AND PREPARATION METHOD THEREOF

CROSS REFERENCE TO RELATED APPLICATIONS

This application is the U.S. National Phase of International Application No. PCT/CN2013/073165, filed Mar. 26, 2013, designating the U.S. and published in Chinese as WO 2014/056304 A1 on Apr. 17, 2014 which claims the benefit of Chinese Patent Application No 201210382696.X, filed Oct. 10, 2012.

Any and all applications for which a foreign or domestic priority claim is identified here or in the Application Data Sheet as filed with the present application are hereby incorporated by reference under 37 CFR 1.57.

FIELD

The application relates to the polymer medicine field, especially to a cisplatin complex and the preparation method thereof.

BACKGROUND

Cisplatin (cis-diamminedichloroplatinum, abbreviated as CDDP) is a metal complex having anti-cancer activity, which is discovered by B. Rosenborg et al. in 1965 for the first time. CDDP has the characteristics such as a wide anti-cancer spectrum, a strong effect, a synergism effect with various antineoplastic drugs, and no cross resistance. Therefore, CDDP is one of the most common drug used in the combination chemotherapy. Currently, CDDP has good effect for treating genital system tumor, malignant lymphoma, cancer in head and neck, bladder carcinoma, lung cancer, and the like. CDDP is invalid in oral administration. The clinical applying method is generally the administration in a manner of intravenous drip. After the intravenous injection, CDDP rapidly disappears from the blood plasma, and rapidly distributes all over the body, especially, mostly distributes in liver, kidney, large and small intestine and skin, therefore the toxic side effect is large. For example, it may cause renal toxicity, bone marrow depression and gastrointestinal tract side effect, and the like. Meanwhile, the half life of CDDP in blood is short, therefore the ratio of it arriving at the focus is very low, and the drug efficiency is low.

In order to prolong the half life of the drug in blood, reduce the nonspecific adsorption effect between the drug and proteins so as to improve the drug efficiency, a general method is to use a polymer material as the carrier for delivering the drug. Recently, micrometer and nanometer sized polymer carriers are rapidly developed, such as micelles, vesicles and nano particles. These types of polymer carriers may effectively distribute the drug molecules therein, and by using various response manners of the carriers, the delivery and controlled release of the drug is achieved. The internal environment of the tumor cell generally appears as "three high factors and one low factor", i.e., a low oxygen level, a low sugar level, and a low pH value, and a high glutathione concentration, wherein the low pH value is especially prominent. The pH value of endosome and lysosome in advanced stage may be as low as 5.0 (Advanced Functional Materials, 19(22): 3580~3589). In addition, the tumor tissue has the characteristics of abundant blood vessels, a relatively broad vascular wall gap, a poor structural integrity, lose of lymphatic return, and the like, such that a high molecule substance and lipid granule have high permeability and retention. Therefore, nanometer to micrometer sized drug carrier systems have substantively "improved effect of penetration and retention", that is, EPR effect. Using the passive targeting manner of EPR effect, the drug can be effectively concentrated in the tumor tissue, meanwhile the toxic and side effect on the non-focus portion can be decreased.

It is disclosed in the prior art various methods of developing CDDP formulation using a polymer carrier for carrying the drug. For example, Kataoka et al. uses CDDP complexed with polyethylene glycol-b-polyglutamic acid to prepare micelles (NC-6004), which drug enters II stage of the clinical test. However, the obtained micelles are formed by the crosslinking effect between the polyamino acid side chains, so that lyophilized powder obtained after lyophilizing the complex obtained by the method is difficult to be redissolved. Stenzel et al. introduces mercapto acetic acid and mercapto succinic acid into the side chain of the polymer using a "mercapto-alkynyl" and "mercapto-alkenyl" Click reaction, obtaining a CDDP complex (Biomacromolecules 12(5): 1738-1751). This complex has good dissolvability. However, the biocompatibility of the polymer used as the carrier is poor, which cannot be degraded. Therefore, the further use thereof is limited.

SUMMARY

The technical problem to be solved by the present disclosure is to provide a CDDP complex, in which CDDP is carried through a chelation effect, the carrier material has good biocompatibility and good dissolvability, and the CDDP complex is stable under physiological condition, and the release of the CDDP has pH value sensitivity.

DETAILED DESCRIPTION OF CERTAIN EMBODIMENTS OF THE INVENTION

The present disclosure provides a CDDP complex, formed by complexation of CDDP and a polymer having a structure of Formula (I),

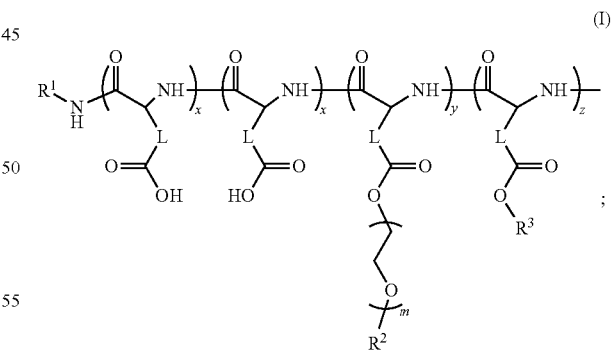

in formula (I), $R^1$ is independently selected from a C2 to C10 linear alkyl group, a C3 to C10 branched alkyl group, a phenyl group or a group of R'—CO—, where R' is independently selected from a C2 to C10 linear alkyl group, a C3 to C10 branched alkyl group or a phenyl group;

$R^2$ is independently selected from a hydrogen atom, a C1 to C20 alkyl group or a substituted C1 to C20 alkyl group;

$R^3$ is independently selected from a hydrogen atom or a cation;

L is independently selected from —CH$_2$— or —CH$_2$—CH$_2$—;

m is a polymerization degree, where 40≤m≤250; and x, y, and z are polymerization degrees, where 10≤2x+y+z≤5000, 5%≤y/(2x+y+z)≤80%.

Preferably, the R$^2$ is independently selected from a hydrogen atom, a C1 to C10 alkyl group or a substituted C1 to C10 alkyl group, where the substituent for the substituted alkyl group is one or more selected from a ketal, an acetal, a hydroxyl group, an aldehyde group, an amino group, a mercapto group, and a glycosyl residue;

R$^3$ is independently selected from a hydrogen atom, a metal cation or an organic cation.

Preferably, R$^3$ is independently selected from a hydrogen atom, a sodium ion, a potassium ion, a magnesium subgroup, an ammonium ion or an amino acid ion.

Preferably, 30≤2x+y+z≤300, and 5%≤y/(2x+y+z)≤50%.

Preferably, the R$^1$ is a C6 alkyl group, R$^2$ is a methyl group, R$^3$ is a hydrogen atom or a sodium ion, and L is —CH$_2$—CH$_2$—.

Correspondingly, the present disclosure provides a preparation method of a CDDP complex, comprising the step of subjecting CDDP to a coordination reaction with a polymer having a structure of Formula (I) in an aqueous medium, to form the CDDP complex;

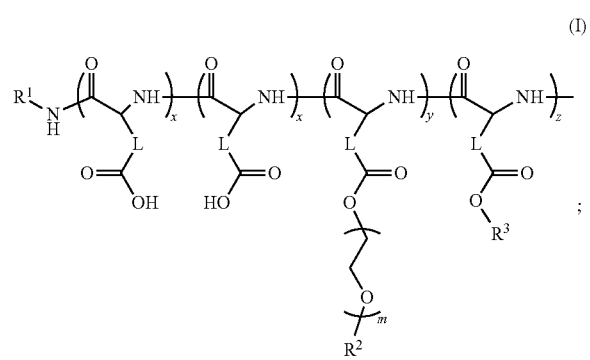

(I)

in formula (I), R$^1$ is independently selected from a C2 to C10 linear alkyl group, a C3 to C10 branched alkyl group, a phenyl group or a group of R'—CO—, where R' is independently selected from a C2 to C10 linear alkyl group, a C3 to C10 branched alkyl group or a phenyl group;

R$^2$ is independently selected from a hydrogen atom, a C1 to C20 alkyl group or a substituted C1 to C20 alkyl group;

R$^3$ is independently selected from a hydrogen atom or a cation;

L is independently selected from —CH$_2$— or —CH$_2$—CH$_2$—;

m is a polymerization degree, where 40≤m≤250; and x, y, and z are polymerization degrees, where 10≤2x+y+z≤5000, 5%≤y/(2x+y+z)≤80%.

Preferably, the molar ratio between the carboxyl group of the polymer having a structure of Formula (I) and Pt in the CDDP is less than 10.

Preferably, the aqueous medium is water, physiological saline, a buffer solution, a tissue culture solution, or a body fluid.

Preferably, the polymer having a structure of Formula (I) is prepared according to a method comprising:

subjecting a polymer having a structure of Formula (II) and a polymer having a structure of Formula (III) to a graft reaction in the presence of both a dehydrating agent and a catalyst, to obtain the polymer having a structure of Formula (I);

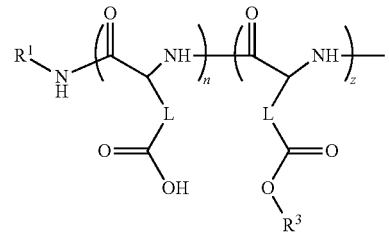

(II)

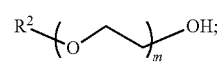

(III)

in Formula (II), R$^1$ is independently selected from a C2 to C10 linear alkyl group, a C3 to C10 branched alkyl group, a phenyl group or a group of R'—CO—, where R' is independently selected from a C2 to C10 linear alkyl group, a C3 to C10 branched alkyl group or a phenyl group;

R$^3$ is independently selected from a hydrogen atom or a cation;

L is independently selected from —CH$_2$— or —CH$_2$—CH$_2$—; and each of n, z is a polymerization degree, where 10≤n+z≤5000;

in Formula (III), R$^2$ is independently selected from a hydrogen atom, a C1 to C20 alkyl group or a substituted C1 to C20 alkyl group; and in is a polymerization degree, where 40≤m≤250.

Preferably, the dehydrating agent is one or more of 1-(3-dimethyl aminopropyl)-3-ethylcarbodiimide hydrochloride, N,N-diisopropyl carbodiimide, and N,N'-dicyclohexyl carbodiimide.

Comparing with the prior art, it is prepared in the present disclosure a CDDP complex using CDDP and the polymer having a structure of Formula (I). The polymer is formed by grafting a polyethylene glycol with a poly(α-glutamic acid) homopolymer, a poly(α, β-aspartic acid) homopolymer, or a copolymer of α-glutamic acid and α, β-aspartic acid. Therefore, the prepared CDDP complex has a good biocompatibility and is degradable. Because the polymer is grafted on the side chain thereof with a polyethylene glycol, prepared CDDP complex has good dissolvability. Meanwhile, in the CDDP complex provided by the present disclosure, the main chain of the polymer is hydrophobic amino acid chain segment, and the side chain is hydrophilic polyethylene glycol chain segment, therefore, when it is dissolved in an aqueous medium, the CDDP is protected by both the hydrophilic polyethylene glycol chain segment and the hydrophobic amino acid chain segment, which can effectively avoid a sudden release of the CDDP due to the influence of the blood circulation system after intravenous injection, thus improving the stability of the CDDP complex. In addition, the carboxyl group contained in the CDDP complex provided by the present disclosure has pH value sensitivity, and tends to be deprotonated in a low pH environment, which is advantageous for promoting the release of the drug, and improving the curative effect of the drug.

FIGURES

SPECIFIC EMBODIMENTS

Figure 1:
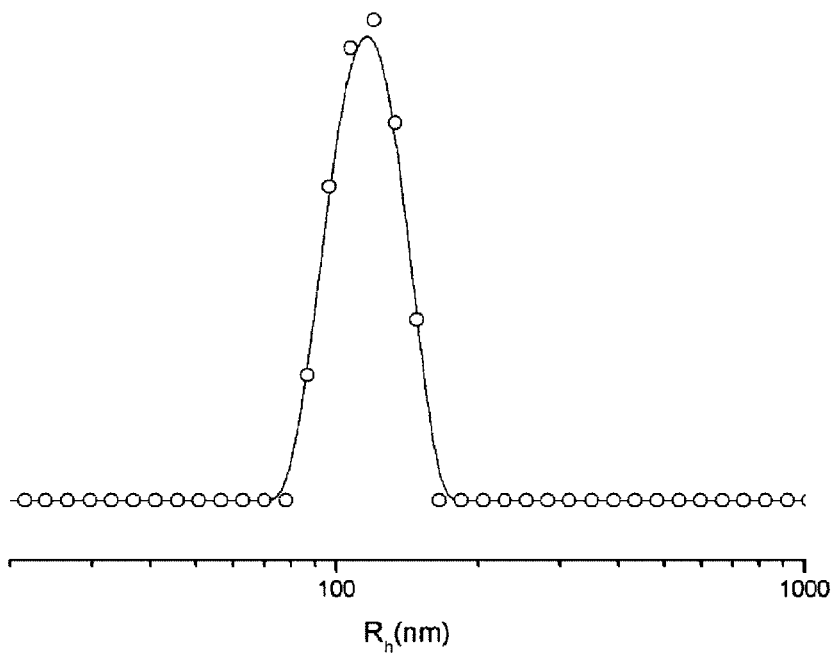
FIG. 1 is a radius distribution diagram of the hydrodynamic radius of the CDDP complex prepared in Example 11 of the present disclosure.

The present disclosure provides a CDDP complex, which is formed by complexation of CDDP and a polymer having a structure of Formula (I),

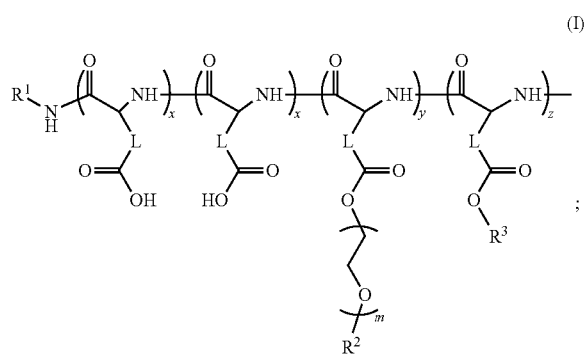

(I)

in formula (I), $R^1$ is independently selected from a C2 to C10 linear alkyl group, a C3 to C10 branched alkyl group, a phenyl group or a group of R'—CO—, where R' is independently selected from a C2 to C10 linear alkyl group, a C3 to C10 branched alkyl group or a phenyl group, $R^1$ is preferably a C3 to C8 linear alkyl group, a C4 to C8 branched alkyl group, a phenyl group, more preferably a C6 alkyl group;

$R^2$ is independently selected from a hydrogen atom, a C1 to C20 alkyl group or a substituted C1 to C20 alkyl group, preferably a hydrogen atom, a C1 to C10 alkyl group or a substituted C1 to C10 alkyl group. The substituent for the substituted alkyl group is one or more selected from a ketal, an acetal, a hydroxyl group, an aldehyde group, an amino group, a mercapto group, and a glycosyl residue;

$R^3$ is independently selected from a hydrogen atom or a cation, preferably a hydrogen atom, a metal cation or an organic cation, more preferably a hydrogen atom, a sodium ion, a potassium ion, a magnesium subgroup, an ammonium ion or an amino acid ion, most preferably a hydrogen atom or a sodium ion;

L is independently selected from —$CH_2$— or —$CH_2$—$CH_2$—;

m is a polymerization degree, where $40 \leq m \leq 250$, preferably $45 \leq m \leq 200$; and x, y, and z are polymerization degrees, where $10 \leq 2x+y+z \leq 5000$, preferably $30 \leq 2x+y+z \leq 300$, more preferably $50 \leq 2x+y+z \leq 250$; $5\% \leq y/(2x+y+z) \leq 80\%$, preferably $5\% \leq y/(2x+y+z) \leq 50\%$.

In the present disclosure, a coordination effect takes place between the CDDP and two carboxyl groups of the polymer, which may be an intramolecular coordination or an intermolecular coordination, and is not specially limited in the present disclosure.

In the present disclosure, preferably, in the polymer having a structure of Formula (I), $R^1$ is a n-hexyl group, $R^2$ is a methyl group, $R^3$ is a hydrogen atom, and L is —$CH_2$—. At this time, the polymer has a structure of Formula (I-a),

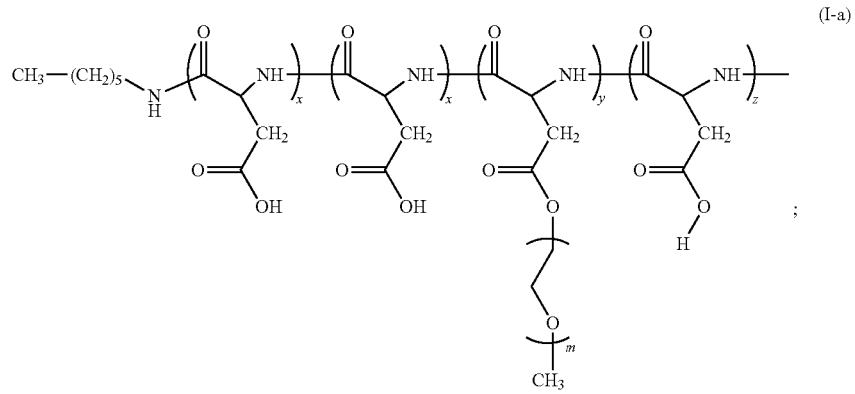

(I-a)

wherein, in is a polymerization degree, where $40 \leq m \leq 250$, preferably $45 \leq m \leq 200$; and x, y, and z are polymerization degrees, where $10 \leq 2x+y+z \leq 5000$, preferably $30 \leq 2x+y+z \leq 300$, more preferably $50 \leq 2x+y+z \leq 250$; $5\% \leq y/(2x+y+z) \leq 80\%$, preferably $5\% \leq y/(2x+y+z) \leq 50\%$.

In the present disclosure, preferably, in the polymer having a structure of Formula (I), $R^1$ is a n-hexyl group, $R^2$ is a methyl group, $R^3$ is a hydrogen atom, and L is —$CH_2$—$CH_2$—. At this time, the polymer has a structure of Formula (I-b),

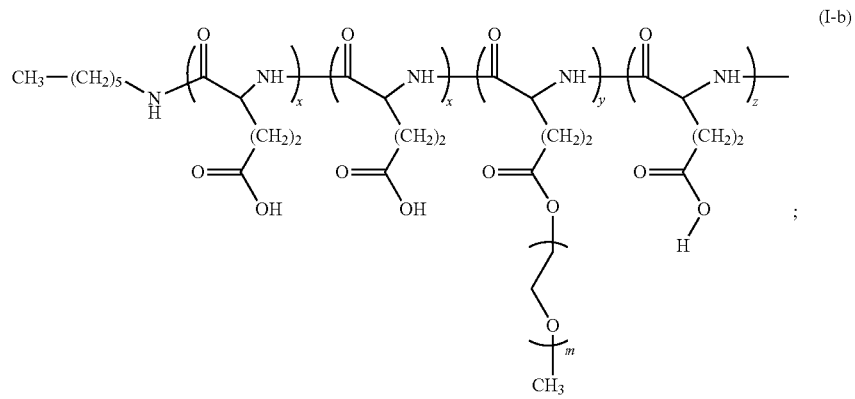

wherein, in is a polymerization degree, where $40 \leq m \leq 250$, preferably $45 \leq m \leq 200$; and x, y, and z are polymerization degrees, where $10 \leq 2x+y+z \leq 5000$, preferably $30 \leq 2x+y+z \leq 300$, more preferably $50 \leq 2x+y+z \leq 250$; $5\% \leq y/(2x+y+z) \leq 80\%$, preferably $5\% \leq y/(2x+y+z) \leq 50\%$.

In the present disclosure, preferably, in the polymer having a structure of Formula (I), $R^1$ is a n-hexyl group, $R^2$ is a hydrogen atom, $R^3$ is a hydrogen atom, and L is —$CH_2$—. At this time, the polymer has a structure of Formula (I-c),

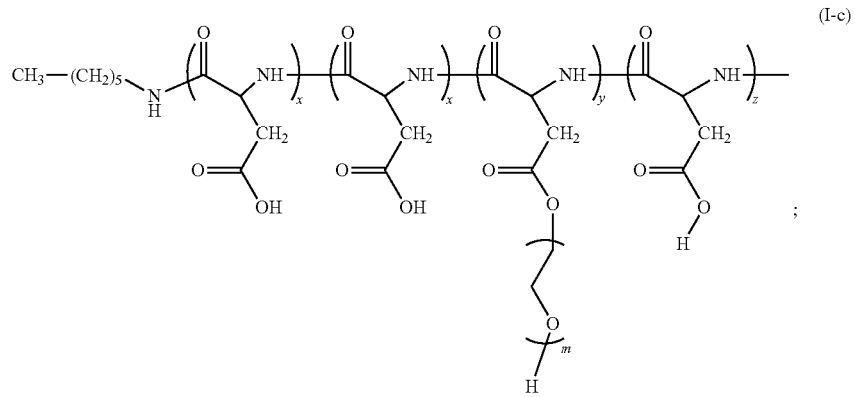

wherein, in is a polymerization degree, where $40 \leq m \leq 250$, preferably $45 \leq m \leq 200$; and x, y, and z are polymerization degrees, where $10 \leq 2x+y+z \leq 5000$, preferably $30 \leq 2x+y+z \leq 300$, more preferably $50 \leq 2x+y+z \leq 250$; $5\% \leq y/(2x+y+z) \leq 80\%$, preferably $5\% \leq y/(2x+y+z) \leq 50\%$.

In the present disclosure, preferably, in the polymer having a structure of Formula (I), $R^1$ is a n-hexyl group, $R^2$ is a hydrogen atom, $R^3$ is a hydrogen atom, and L is —$CH_2$—$CH_2$—. At this time, the polymer has a structure of Formula (I-d),

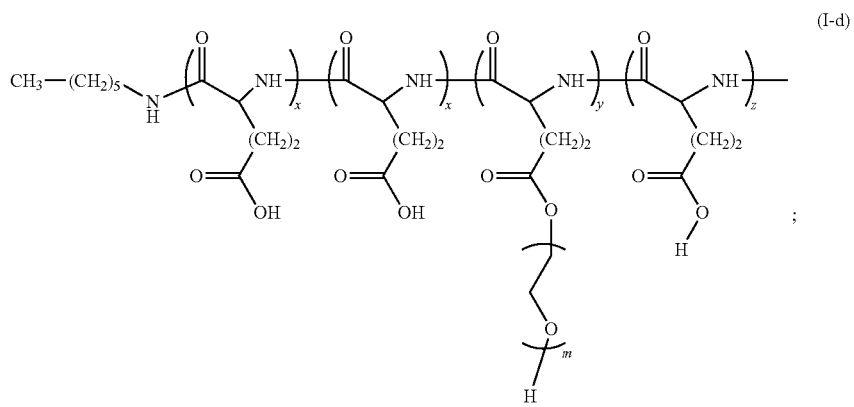

(I-d)

wherein, in is a polymerization degree, where $40 \leq m \leq 250$, preferably $45 \leq m \leq 200$; and x, y, and z are polymerization degrees, where $10 \leq 2x+y+z \leq 5000$, preferably $30 \leq 2x+y+z \leq 300$, more preferably $50 \leq 2x+y+z \leq 250$; $5\% \leq y/(2x+y+z) \leq 80\%$, preferably $5\% \leq y/(2x+y+z) \leq 50\%$.

The present disclosure also provides a preparation method of a CDDP complex, comprising the step of subjecting CDDP to a coordination reaction with a polymer having a structure of Formula (I) in the aqueous medium, to form a CDDP complex;

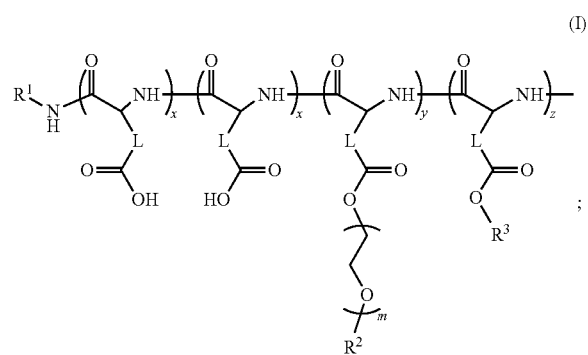

(I)

In formula (I), $R^1$ is independently selected from a C2 to C10 linear alkyl group, a C3 to C10 branched alkyl group, a phenyl group or a group of R'—CO—, where R' is independently selected from a C2 to C10 linear alkyl group, a C3 to C10 branched alkyl group or a phenyl group, and $R^1$ is preferably a C3 to C8 linear alkyl group, a C4 to C8 branched alkyl group, a phenyl group, more preferably a C6 alkyl group;

$R^2$ is independently selected from a hydrogen atom, a C1 to C20 alkyl group or a substituted C1 to C20 alkyl group, preferably a hydrogen atom, a C1 to C10 alkyl group or a substituted C1 to C10 alkyl group, The substituent for the substituted alkyl group is one or more selected from a ketal, an acetal, a hydroxyl group, an aldehyde group, an amino group, a mercapto group, and a glycosyl residue;

$R^3$ is independently selected from a hydrogen atom or a cation, preferably a hydrogen atom, a metal cation or an organic cation, more preferably a hydrogen atom, a sodium ion, a potassium ion, a magnesium subgroup, an ammonium ion or an amino acid ion, most preferably a hydrogen atom or a sodium ion;

L is independently selected from —$CH_2$— or —$CH_2$—$CH_2$—;

m is a polymerization degree, where $40 \leq m \leq 250$, preferably $45 \leq m \leq 200$; and x, y, and z are polymerization degrees, where $10 \leq 2x+y+z \leq 5000$, preferably $30 \leq 2x+y+z \leq 300$, more preferably $50 \leq 2x+y+z \leq 250$; $5\% \leq y/(2x+y+z) \leq 80\%$, preferably $5\% \leq y/(2x+y+z) \leq 50\%$.

In the present disclosure, the polymer having a structure of Formula (I) is the carrier for carrying CDDP. The Pt in CDDP and the carboxyl groups of the polymer form a ring structure via a coordination bond, whereby the CDDP complex is obtained. Preferably, all CDDP molecules form coordination bonds with the polymer, but it is not limited to the case where all CDDP molecules form coordination bonds with the carboxyl groups of the polymer, and may also comprise the case where a part of CDDP molecules are carried on the carrier material by a hydrophobic effect or any other physical manner; the coordination between CDDP and the polymer may be an intermolecular coordination or an intramolecular coordination, which is not specially limited in the present disclosure. The molar ratio between the carboxyl group of the polymer having a structure of Formula (I) and Pt in the CDDP is less than 10, preferably larger than 0.3 and less than 10, more preferably larger than 0.5 and less than 8.

In the preparation method of the CDDP complex of the present disclosure, preferably, the polymer having a structure of Formula (I) is dissolved in an aqueous medium under the condition of shielding light, followed by adjusting pH value, adding CDDP, and subjecting to a coordination reaction, and thereby CDDP complex micelles are obtained after dialysis. The aqueous medium is preferably water, physiological saline, a buffer solution, a tissue culture solution or a body fluid, more preferably double distilled water. The pH value of the double distilled water is preferably 6.5 to 8.5, more preferably 7.0 to 8.0. The concentration of carboxyl group of the polymer in the aqueous medium is preferably 0.1 mM to 100 mM, more preferably 1 mM to 60 mM, most preferably 2 mM to 20 mM. After the polymer is dissolved in the aqueous medium, the pH value thereof is preferably adjusted to 6.0 to 10.0, more preferably 8.0 to 9.0; and then CDDP is added to carry out a coordination reaction. The time of the coordination reaction is preferably 24 to 72 hours, more preferably 48 to 72 hours; the temperature of the coordination reaction is preferably 20° C. to 40° C. After the coordination reaction is finished, the product is dialyzed for a time period of from 24 to 72 hours, preferably 24 to 48 hours; and after 6 to 12 times of replacement of dialysing liquid, the CDDP complex micelles are obtained.

According to the preparation method of the CDDP complex of the present disclosure, the obtained CDDP complex is presents in form of micelles in the aqueous medium. The hydrodynamic radius of the micelles is preferably 10 nm to 2000 nm, more preferably 10 nm to 300 nm.

Because the CDDP complex in form of micelles is not disadvantageous for preservation, it is preferably subjected to a post treatment to obtain a lyophilized powder of the CDDP complex. The post treatment preferably comprises lyophilizing under a sterile condition to obtain CDDP complex lyophilized powder. During the lyophilizing process, a small amount of lyophilizing protecting agent may be added, such as one or more of a small molecular amino acid, maltose, sucrose, lactose, glucose, and mannitol. The addition of the protecting agent may effectively avoid the aggregation of the complex carrying the drug.

When the CDDP complex is prepared in the present disclosure, the polymer having a structure of Formula (I) is used as a raw material, to take place a coordination reaction with CDDP in an aqueous medium. The molar ratio between the carboxyl groups of the polymer having a structure of Formula (I) and Pt in CDDP is preferably larger than 0.3 and less than 10. The present disclosure does not specially limit the form of the polymer having a structure of Formula (I), but it is preferably a lyophilized powder; the present disclosure does not specially limit the source of the polymer having a structure of Formula (I), but it is preferably prepared according to the following method.

A polymer having a structure of Formula (II) is subjected to a grafting reaction with a polymer having a structure of Formula (III) in the presence of both a dehydrating agent and a catalyst, obtaining the polymer having a structure of Formula (I);

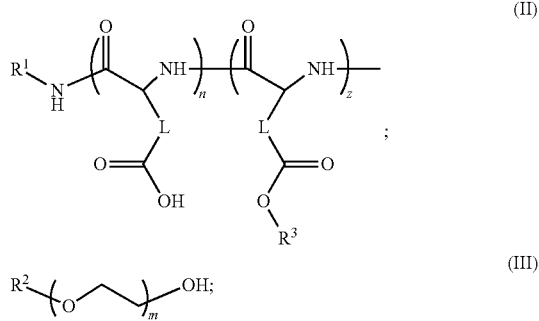

in Formula (II), $R^1$ is independently selected from a C2 to C10 linear alkyl group, a C3 to C10 branched alkyl group, a phenyl group or a group of R'—CO—, where R' is independently selected from a C2 to C10 linear alkyl group, a C3 to C10 branched alkyl group or a phenyl group, $R^1$ is preferably a C3 to C8 linear alkyl group, a C4 to C8 branched alkyl group, a phenyl group, more preferably a C6 alkyl group;

$R^3$ is independently selected from H or a cation, preferably a hydrogen atom, a metal cation or an organic cation, more preferably a hydrogen atom, a sodium ion, a potassium ion, a magnesium subgroup, an ammonium ion or an amino acid ion, most preferably a hydrogen atom or a sodium ion;

L is independently selected from —$CH_2$— or —$CH_2$—$CH_2$—;

each of n, z is a polymerization degree, $10 \leq n+z \leq 5000$, preferably $30 \leq n+z \leq 300$, more preferably $50 \leq n+z \leq 250$; $5\% \leq z/(n+z) \leq 80\%$, preferably $5\% \leq z/(n+z) \leq 50\%$;

in Formula (III), $R^2$ is independently selected from a alkyl group or a substituted alkyl group, preferably a hydrogen atom, a C1 to C10 alkyl group or a substituted C1 to C10 alkyl group, The substituent for the substituted alkyl is one or more selected from a ketal, an acetal, a hydroxyl group, an aldehyde group, an amino group, a mercapto group, and a glycosyl residue;

m is a polymerization degree, $40 \leq m \leq 250$, preferably $45 \leq m \leq 200$.

The reaction for preparing the polymer having a structure of Formula (I) of the present disclosure is preferably carried out under the protection of an inert gas. The polymer having a structure of Formula (II) and the polymer having a structure of Formula (III) are dissolved with a solvent, and then subjected to a grafting reaction under the action of a dehydrating agent and a catalyst, thereby the polymer having a structure of Formula (I) is obtained. The reaction temperature is preferably room temperature; the reaction time is preferably 3 to 5 days; the inert gas is preferably nitrogen gas, and the time duration of introducing nitrogen is preferably 0.5 to 1 hours; the solvent is preferably dimethyl sulfoxide, N,N-dimethyl formamide or dioxane, more preferably dimethyl sulfoxide; the dehydrating agent is preferably one or more of 1-(3-dimethyl aminopropyl)-3-ethylcarbodiimide hydrochloride or N,N-diisopropyl carbodiimide or N,N'-dicyclohexyl carbodiimide, more preferably N,N-diisopropyl carbodiimide; the catalyst is preferably 4-dimethyl pyridine. After the polymer having a structure of Formula (I) is obtained, it is preferably dialyzed for 72 hours, during which period dialysing liquid is replaced for 12 times, and then lyophilized, so as to obtain the lyophilized powder of the polymer having a structure of Formula (I).

In the present disclosure, during the preparation of the polymer having a structure of Formula (I), the polymer having a structure of Formula (II) and the polymer having a structure of Formula (III) are used as the raw materials; the source of the block copolymer having a structure of Formula (II) or Formula (III) is not specially limited in the present disclosure, wherein, Formula (II) is preferably prepared according to the following method.

γ-benzyl-L-glutamic acid or γ-benzyl-L-aspartic acid is reacted with triphosgene, to form γ-benzyl-L-glutamic acid-N-carboxylic acid anhydride monomer or γ-benzyl-L-aspartic acid-N-carboxylic acid anhydride monomer. In the present disclosure, it is preferred that, under an inert gas condition, γ-benzyl-L-glutamic acid or γ-benzyl-L-aspartic acid is added into tetrahydrofuran, and then triphosgene is added to carry out a reaction. After the reaction, sedimentation in a solvent occurs, and a solid is obtained, which is then recrystallized and dried, obtaining γ-benzyl-L-glutamic acid-N-carboxylic acid anhydride monomer or γ-benzyl-L-aspartic acid-N-carboxylic acid anhydride monomer. The solvent is preferably petroleum ether or n-hexane; the inert gas is preferably nitrogen gas. In the present disclosure, the manners of the sedimentation, recrystallization and drying are not limited, and any of the manners of sedimentation, recrystallization and drying known by a person skilled in the art can be used.

After γ-benzyl-L-glutamic acid-N-carboxylic acid anhydride monomer or γ-benzyl-L-aspartic acid-N-carboxylic acid anhydride monomer is obtained, it is subjected to a ring-opening polymerization reaction under the action of an initiator having a structure of formula (IV). After benzyl group is removed, an amino acid copolymer of Formula (II) is obtained. Or, γ-benzyl-L-glutamic acid-N-carboxylic acid anhydride monomer or γ-benzyl-L-aspartic acid-N-carboxylic acid anhydride monomer is subjected to a ring-opening polymerization reaction under the action of an initiator having a structure of Formula (IV), and after removing benzyl group, mixed with a sodium ion, a potassium ion, or a magnesium ion, to obtain the amino acid copolymer of Formula (II);

$R^1$—$NH_2$ (IV);

in Formula (IV), $R^1$ is independently selected from a C2 to C10 linear alkyl group, a C3 to C10 branched alkyl group, a phenyl group or a group of R'—CO—, where R' is independently selected from a C2 to C10 linear alkyl group, a C3 to C10 branched alkyl group or a phenyl group, $R^1$ is preferably a C3 to C8 linear alkyl group, a C4 to C8 branched alkyl group, a phenyl group, more preferably a C6 alkyl group. It is preferable in the present disclosure that, under an inert gas condition, a solution of an initiator having a structure of Formula (IV) in dimethyl formamide is added into a solution of γ-benzyl-L-glutamic acid-N-carboxylic acid anhydride monomer or γ-benzyl-L-aspartic acid-N-carboxylic acid anhydride monomer in dimethyl formamide. After the reaction, the product is deposited in the solvent. A solid is obtained after filtration. After drying and removing the benzyl protecting group, the amino acid copolymer of Formula (II) is obtained. The solvent is preferably diethyl ether; the inert gas is preferably nitrogen gas; the manners of the sedimentation, filtrating and drying are not limited in the present disclosure, and any of the manners of sedimentation, filtrating and drying known by a person skilled in the art can be used.

In order to further understanding the present disclosure, the CDDP complex provided by the present disclosure and the preparation method thereof are described below with reference to Examples.

Example 1

Under a dry inert gas condition, 10 g of γ-benzyl-L-glutamic acid were added into 100 ml of anhydrous tetrahydrofuran, and reacted with 6.5 g of triphosgene. Petroleum ether was then added for sedimentating, to obtain a solid. After recrystallization and drying, 7.85 g of γ-benzyl-L-glutamic acid-N-carboxylic acid anhydride (BLG-NCA) monomer were finally obtained. Under an inert gas condition, a solution of n-hexyl amine in dimethyl formamide (DMF) was added into a solution of BLG-NCA in DMF, wherein the molar ratio between n-hexyl amine and γ-benzyl-L-glutamic acid-N-carboxylic acid anhydride (BLG-NCA) was 1:160. After the reaction, diethyl ether was added for sedimentating, to obtain a solid after filtration. After drying, a glutamic acid copolymer having a benzyl protecting group and a polymerization degree of 160 was obtained. After the protecting group was removed, a glutamic acid copolymer having a structure of formula (II) and a polymerization degree of 160 was obtained, denoted as $P(Glu)_{160}$.

Into a dried reaction flask, 1.010 g of the above prepared $P(Glu)_{160}$, 1.010 g of a polyethylene glycol monomethyl ether with a number-average molecular weight of 2012, denoted as $mPEG_{45}$, were added, and they were dissolved with 20 mL of dried dimethyl sulfoxide and stirred. Nitrogen gas was introduced for 0.5 hour. Under the conditions of room temperature and nitrogen gas protection, 24.7 mg of 4-dimethyl pyridine and 0.31 ml of N,N-diisopropyl carbodiimide were added, and reacted with stirring at room temperature for 3 days, to obtain the product. The product was dialysed for 72 hours, during which period the dialysing liquid was replaced for 12 times. The lyophilized polymer powder having a structure of formula (I-b) was obtained by lyophilizing.

The polymer was subjected to a nuclear magnetic resonance measurement. The calculation results showed that the grafting ratio was 6.25%, and the reaction conversion was 88%. The polymer having a structure of formula (I-b) where y=10 was obtained, denoted as $P(Glu)_{160}$-g-$(mPEG_{45})_{10}$.

Example 2

Under a dry inert gas condition, 10 g of γ-benzyl-L-glutamic acid were added into 100 ml of anhydrous tetrahydrofuran, and reacted with 6.5 g of triphosgene. Petroleum ether was then added for sedimentating, to obtain a solid. After recrystallization and drying, 7.34 g of γ-benzyl-L-glutamic acid-N-carboxylic acid anhydride (BLG-NCA) monomer were finally obtained. Under an inert gas condition, a solution of n-hexyl amine in dimethyl formamide (DMF) was added into a solution of BLG-NCA in DMF, wherein the molar ratio between n-hexyl amine and γ-benzyl-L-glutamic acid-N-carboxylic acid anhydride (BLG-NCA) was 1:160. After the reaction, diethyl ether was added for sedimentating, to obtain a solid after filtration. After drying, a glutamic acid copolymer having a benzyl protecting group and a polymerization degree of 160 was obtained. After the protecting group was removed, a glutamic acid copolymer having a structure of formula (II) and a polymerization degree of 160 was obtained, denoted as $P(Glu)_{160}$.

Into a dried reaction flask, 1.012 g of the above prepared $P(Glu)_{160}$, 2.001 g of a polyethylene glycol monomethyl ether with a number-average molecular weight of 1998, denoted as $PEG_{45}$, were added, and they were dissolved with 30 mL of dried dimethyl sulfoxide and stirred. Nitrogen gas was introduced for 0.5 hour. Under the conditions of room temperature and nitrogen gas protection, 49.1 mg of 4-dimethyl pyridine and 0.62 ml of N,N-diisopropyl carbodiimide were added, and reacted with stirring at room temperature for 3 days, to obtain the product. The product was dialysed for 72 hours, during which period the dialysing liquid was replaced for 12 times. The lyophilized polymer powder having a structure of formula (I-d) was obtained by lyophilizing.

The polymer was subjected to a nuclear magnetic resonance measurement. The calculation results showed that the grafting ratio was 12.5%, and the reaction conversion was 87%. The polymer having a structure of formula (I-d) where y=20 was obtained, denoted as $P(Glu)_{160}$-g-$(PEG_{45})_{20}$.

Example 3

Under a dry inert gas condition, 10 g of γ-benzyl-L-glutamic acid were added into anhydrous tetrahydrofuran, and reacted with 6.5 g of triphosgene. Petroleum ether was then added for sedimentating, to obtain a solid. After recrystallization and drying, 8.2 g of γ-benzyl-L-glutamic acid-N-carboxylic acid anhydride (BLG-NCA) monomer were finally obtained. Under an inert gas condition, a solution of n-hexyl amine in dimethyl formamide (DMF) was added into a solution of BLG-NCA in DMF, wherein the molar ratio between n-hexyl amine and γ-benzyl-L-glutamic acid-N-carboxylic acid anhydride (BLG-NCA) was 1:160. After the reaction, diethyl ether was added for sedimentating, to obtain a solid after filtration. After drying, a glutamic acid copolymer having a benzyl protecting group and a polymerization degree of 160 was obtained. After the protecting group was removed, a glutamic acid copolymer having a structure of formula (II) and a polymerization degree of 160 was obtained, denoted as $P(Glu)_{160}$.

Into a dried reaction flask, 0.5000 g of the above prepared $P(Glu)_{160}$, 2.013 g of a polyethylene glycol monomethyl ether with a number-average molecular weight of 2012, denoted as $mPEG_{45}$, were added, and they were dissolved with 25 mL of dried dimethyl sulfoxide and stirred. Nitrogen gas was introduced for 0.5 hour. Under the conditions of room temperature and nitrogen gas protection, 49.2 mg of 4-dimethyl pyridine and 0.63 ml of N,N-diisopropyl carbodiimide were added, and reacted with stirring at room temperature for 3 days, to obtain the product. The product was dialysed for 72 hours, during which period the dialysing liquid was replaced for 12 times. The lyophilized polymer powder having a structure of formula (I-b) was obtained by lyophilizing.

The polymer was subjected to a nuclear magnetic resonance measurement. The calculation results showed that the grafting ratio was 25%, and the reaction conversion was 85%. The polymer having a structure of formula (I-b) where y=40 was obtained, denoted as $P(Glu)_{160}\text{-g-}(mPEG_{45})_{40}$.

Example 4

Under a dry inert gas condition, 10 g of γ-benzyl-L-glutamic acid were added into 100 ml of anhydrous tetrahydrofuran, and reacted with 6.5 g of triphosgene. Petroleum ether was then added for sedimentating, to obtain a solid. After recrystallization and drying, 7.8 g of γ-benzyl-L-glutamic acid-N-carboxylic acid anhydride (BLG-NCA) monomer were finally obtained. Under an inert gas condition, a solution of n-hexyl amine in dimethyl formamide (DMF) was added into a solution of BLG-NCA in DMF, wherein the molar ratio between n-hexyl amine and γ-benzyl-L-glutamic acid-N-carboxylic acid anhydride (BLG-NCA) was 1:160. After the reaction, diethyl ether was added for sedimentating, to obtain a solid after filtration. After drying, a glutamic acid copolymer having a benzyl protecting group and a polymerization degree of 160 was obtained. After the protecting group was removed, a glutamic acid copolymer having a structure of formula (II) and a polymerization degree of 160 was obtained, denoted as $P(Glu)_{160}$.

Into a dried reaction flask, 0.2520 g of the above prepared $P(Glu)_{160}$, 2.005 g of a polyethylene glycol monomethyl ether with a number-average molecular weight of 1998, denoted as $PEG_{45}$ were added, and they were dissolved with 22 mL of dried dimethyl sulfoxide and stirred. Nitrogen gas was introduced for 0.5 hour. Under the conditions of room temperature and nitrogen gas protection, 49.0 mg of 4-dimethyl pyridine and 0.62 ml of N,N-diisopropyl carbodiimide were added, and reacted with stirring at room temperature for 3 days, to obtain the product. The product was dialysed for 72 hours, during which period the dialysing liquid was replaced for 12 times. The lyophilized polymer powder having a structure of formula (I-d) was obtained by lyophilizing.

The polymer was subjected to a nuclear magnetic resonance measurement. The calculation results showed that the grafting ratio was 50%, and the reaction conversion was 83%. The polymer having a structure of formula (I-d) where y=80 was obtained, denoted as $P(Glu)_{160}\text{-g-}(PEG_{45})_{80}$.

Example 5

Under a dry inert gas condition, 10 g of γ-benzyl-L-glutamic acid were added into anhydrous tetrahydrofuran, and sufficiently reacted with 6.5 g of triphosgene. Petroleum ether was then added for sedimentating, to obtain a solid. After recrystallization and drying, 7.65 g of γ-benzyl-L-glutamic acid-N-carboxylic acid anhydride (BLG-NCA) monomer were finally obtained. Under an inert gas condition, a solution of n-hexyl amine in dimethyl formamide (DMF) was added into a solution of BLG-NCA in DMF, wherein the molar ratio between n-hexyl amine and γ-benzyl-L-glutamic acid-N-carboxylic acid anhydride (BLG-NCA) was 1:50. After the reaction, diethyl ether was added for sedimentating, to obtain a solid after filtration. After drying, a glutamic acid copolymer having a benzyl protecting group and a polymerization degree of 50 was obtained. After the protecting group was removed, a glutamic acid copolymer having a structure of formula (II) and a polymerization degree of 50 was obtained, denoted as $P(Glu)_{50}$.

Into a dried reaction flask, 0.5000 g of the above prepared $P(Glu)_{50}$, 2.010 g of a polyethylene glycol monomethyl ether with a number-average molecular weight of 4432, denoted as $mPEG_{100}$, were added, and they were dissolved with 25 mL of dried dimethyl sulfoxide and stirred. Nitrogen gas was introduced for 0.5 hour. Under the conditions of room temperature and nitrogen gas protection, 49.1 mg of 4-dimethyl pyridine and 0.63 ml of N,N-diisopropyl carbodiimide were added, and reacted with stirring at room temperature for 3 days, to obtain the product. The product was dialysed for 72 hours, during which period the dialysing liquid was replaced for 12 times, and the lyophilized polymer powder having a structure of formula (I-b) was obtained by lyophilizing.

The polymer was subjected to a nuclear magnetic resonance measurement. The calculation results showed that the grafting ratio was 10%, and the reaction conversion was 80%. The polymer having a structure of formula (I-b) where y=5 was obtained, denoted as $P(Glu)_{50}\text{-g-}(mPEG_{100})_5$.

Example 6

Under a dry inert gas condition, 10 g of γ-benzyl-L-glutamic acid were added into 100 ml of anhydrous tetrahydrofuran, and reacted with 6.5 g of triphosgene. Petroleum ether was then added for sedimentating, to obtain a solid. After recrystallization and drying, 8.25 g of γ-benzyl-L-glutamic acid-N-carboxylic acid anhydride (BLG-NCA) monomer were finally obtained. Under an inert gas condition, a solution of n-hexyl amine in dimethyl formamide (DMF) was added into a solution of BLG-NCA in DMF, wherein the molar ratio between n-hexyl amine and γ-benzyl-L-glutamic acid-N-carboxylic acid anhydride (BLG-NCA) was 1:50. After the reaction, diethyl ether was added for sedimentating, to obtain a solid after filtration. After drying, a glutamic acid copolymer having a benzyl protecting group and a polymerization degree of 50 was obtained. After the protecting group was removed, a glutamic acid copolymer having a structure of formula (II) and a polymerization degree of 50 was obtained, denoted as $P(Glu)_{50}$.

Into a dried reaction flask, 0.500 g of $P(Glu)_{50}$, 5.000 g of a polyethylene glycol monomethyl ether with a number-average molecular weight of 8818, denoted as $mPEG_{200}$, were added, and they were dissolved with 55 mL of dried dimethyl sulfoxide and stirred. Nitrogen gas was introduced for 0.5 hour. Under the conditions of room temperature and nitrogen gas protection, 61.4 mg of 4-dimethyl pyridine and 0.79 ml of N,N-diisopropyl carbodiimide were added, and reacted with stirring at room temperature for 3 days, to obtain the product. The product was dialysed for 72 hours, during which period the dialysing liquid was replaced for 12 times. The lyophilized polymer powder having a structure of formula (I-d) was obtained by lyophilizing.

The polymer was subjected to a nuclear magnetic resonance measurement. The calculation results showed that the grafting ratio was 13%, and the reaction conversion was 76%. The polymer having a structure of formula (I-d) where y=7 was obtained, denoted as $P(Glu)_{50}$-g-$(mPEG_{200})_7$.

Example 7

Under a dry inert gas condition, 10 g of γ-benzyl-L-glutamic acid were added into 100 ml of anhydrous tetrahydrofuran, and reacted with 6.5 g of triphosgene. Petroleum ether was then added for sedimentating, to obtain a solid. After recrystallization and drying, 8.16 g of γ-benzyl-L-glutamic acid-N-carboxylic acid anhydride (BLG-NCA) monomer were finally obtained. Under an inert gas condition, a solution of n-hexyl amine in dimethyl formamide (DMF) was added into a solution of BLG-NCA in DMF, wherein the molar ratio between n-hexyl amine and γ-benzyl-L-glutamic acid-N-carboxylic acid anhydride (BLG-NCA) was 1:250. After the reaction, diethyl ether was added for sedimentating, to obtain a solid after filtration. After drying, a glutamic acid copolymer with a polymerization degree of 250 and a benzyl protecting group was obtained. After the protecting group was removed, a glutamic acid copolymer having a structure of formula (II) and a polymerization degree of 250 was obtained, denoted as $P(Glu)_{250}$.

Into a dried reaction flask, 0.500 g of above prepared $P(Glu)_{250}$, 3.000 g of a polyethylene glycol monomethyl ether with a number-average molecular weight of 4418, denoted as $mPEG_{100}$, were added, and they were dissolved with 35 mL of dried dimethyl sulfoxide and stirred. Nitrogen gas was introduced for 0.5 hour. Under the conditions of room temperature and nitrogen gas protection, 73.7 mg of 4-dimethyl pyridine and 0.95 ml of N,N-diisopropyl carbodiimide were added, and reacted with stirring at room temperature for 3 days, to obtain the product. The product was dialysed for 72 hours, during which period the dialysing liquid was replaced for 12 times. The lyophilized polymer powder having a structure of formula (I-d) was obtained by lyophilizing.

The polymer was subjected to a nuclear magnetic resonance measurement. The calculation results showed that the grafting ratio was 15%, and the reaction conversion was 75%. The polymer having a structure of formula (I-d) where y=38 was obtained, denoted as $P(Glu)_{250}$-g-$(mPEG_{100})_{38}$.

Example 8

Under a dry inert gas condition, 10 g of γ-benzyl-L-glutamic acid was added into 100 ml of anhydrous tetrahydrofuran, and reacted with 6.5 g of triphosgene. Petroleum ether was then added for sedimentating, to obtain a solid. After recrystallization and drying, 7.94 g of γ-benzyl-L-glutamic acid-N-carboxylic acid anhydride (BLG-NCA) monomer were finally obtained. Under an inert gas condition, a solution of n-hexyl amine in dimethyl formamide (DMF) was added into a solution of BLG-NCA in DMF, wherein the molar ratio between n-hexyl amine and γ-benzyl-L-glutamic acid-N-carboxylic acid anhydride (BLG-NCA) was 1:250. After the reaction, diethyl ether was added for sedimentating, to obtain a solid after filtration. After drying, a glutamic acid copolymer having a benzyl protecting group and a polymerization degree of 160 was obtained. After the protecting group was removed, a glutamic acid copolymer having a structure of formula (II) and a polymerization degree of 160 was obtained, denoted as $P(Glu)_{160}$.

Into a dried reaction flask, 0.500 g of above prepared $P(Glu)_{250}$, 5.000 g of a polyethylene glycol monomethyl ether with a number-average molecular weight of 8832, $mPEG_{200}$, were added, and they were dissolved with 55 mL of dried dimethyl sulfoxide and stirred. Nitrogen gas was introduced for 0.5 hour. Under the conditions of room temperature and nitrogen gas protection, 61.4 mg of 4-dimethyl pyridine and 0.79 ml of N,N-diisopropyl carbodiimide were added, and reacted with stirring at room temperature for 3 days, to obtain the product. The product was dialysed for 72 hours, during which period the dialysing liquid was replaced for 12 times, and the lyophilized polymer powder having a structure of formula (I-b) was obtained by lyophilizing.

The polymer was subjected to a nuclear magnetic resonance measurement. The calculation results showed that the grafting ratio was 12%, and the reaction conversion was 82%. The polymer having a structure of formula (I-b) where y=30 was obtained, denoted as $P(Glu)_{250}$-g-$(mPEG_{200})_{30}$.

Example 9

Under a dry inert gas condition, 10 g of γ-benzyl-L-aspartic acid were added into 100 ml of anhydrous tetrahydrofuran, and reacted with 7 g of triphosgene. Petroleum ether was then added for sedimentating, to obtain a solid. After recrystallization and drying, 7.02 g of γ-benzyl-L-aspartic acid-N-carboxylic acid anhydride (BAS-NCA) monomer were finally obtained. Under an inert gas condition, a solution of n-hexyl amine in dimethyl formamide (DMF) was added into a solution of BAS-NCA in DMF, wherein the molar ratio between n-hexyl amine and γ-benzyl-L-aspartic acid-N-carboxylic acid anhydride (BAS-NCA) was 1:160. After the reaction, diethyl ether was added for sedimentating, to obtain a solid after filtration. After drying, a glutamic acid copolymer having a benzyl protecting group and a polymerization degree of 160 was obtained. After the protecting group was removed, a glutamic acid copolymer having a structure of formula (II) and a polymerization degree of 160 was obtained, denoted as $P(Asp)_{160}$.

Into a dried reaction flask, 1.500 g of $P(Asp)_{160}$, 2.600 g of a polyethylene glycol monomethyl ether with a number-average molecular weight of 2012, denoted as $mPEG_{45}$, were added, and they were dissolved with 28 mL of dried dimethyl sulfoxide and stirred. Nitrogen gas was introduced for 0.5 hour. Under the conditions of room temperature and nitrogen gas protection, 63.5 mg of 4-dimethyl pyridine and 0.80 ml of N,N-diisopropyl carbodiimide were added, and reacted with stirring at room temperature for 3 days, to obtain the product. The product was dialysed for 72 hours, during which period the dialysing liquid was replaced for 12 times, and the lyophilized polymer powder having a structure of formula (I-a) was obtained by lyophilizing.

The polymer was subjected to a nuclear magnetic resonance measurement. The calculation results showed that the grafting ratio was 10%, and the reaction conversion was 81%. The polymer having a structure of formula (I-a) where y=16 was obtained, denoted as $P(Asp)_{160}$-g-$(mPEG_{45})_{16}$.

Example 10

Under a dry inert gas condition, 10 g of γ-benzyl-L-aspartic acid were added into 100 ml of anhydrous tetrahydrofuran, and reacted with 7 g of triphosgene. Petroleum ether was then added for sedimentating, to obtain a solid.

After recrystallization and drying, 7.25 g of γ-benzyl-L-aspartic acid-N-carboxylic acid anhydride (BAS-NCA) monomer were finally obtained. Under an inert gas condition, a solution of n-hexyl amine in dimethyl formamide (DMF) was added into a solution of BAS-NCA in DMF, wherein the molar ratio between n-hexyl amine and γ-benzyl-L-aspartic acid-N-carboxylic acid anhydride (BAS-NCA) was 1:250. After the reaction, diethyl ether was added for sedimentating, to obtain a solid after filtration. After drying, a glutamic acid copolymer having a benzyl protecting group and a polymerization degree of 250 was obtained. After the protecting group was removed, a glutamic acid copolymer having a structure of formula (II) and a polymerization degree of 250 was obtained, denoted as $P(Asp)_{250}$.

Into a dried reaction flask, 1.210 g of $P(Asp)_{250}$, 6.800 g of a polyethylene glycol monomethyl ether with a number-average molecular weight of 8818, denoted as $mPEG_{200}$, were added, and they were dissolved with 80 mL of dried dimethyl sulfoxide and stirred. Nitrogen gas was introduced for 0.5 hour. Under the conditions of room temperature and nitrogen gas protection, 166 mg of 4-dimethyl pyridine and 2.1 ml of N,N-diisopropyl carbodiimide were added, and reacted with stirring at room temperature for 3 days, to obtain the product. The product was dialysed for 72 hours, during which period the dialysing liquid was replaced for 12 times, and the lyophilized polymer powder having a structure of formula (I-c) was obtained by lyophilizing.

The polymer was subjected to a nuclear magnetic resonance measurement. The calculation results showed that the grafting ratio was 5.2%, and the reaction conversion was 78%. The polymer having a structure of formula (I-c) where y=13 was obtained, denoted as $P(Asp)_{250}$-g-$(mPEG_{45})_{13}$.

Example 11

34.6 mg of $P(Glu)_{160}$-g-$(mPEG_{45})_{10}$ prepared in Example 1 were dissolved in 25 mL of double distilled water. The pH value was adjusted to from 8 to 9. 18.7 mg of CDDP were added, and stirred under the condition of shielding light at 37° C. for 72 h. After removing free CDDP by dialysing with pure water for 24 h, during which time water was replaced for 6 times, micelles of the CDDP complex were obtain. The micells of the CDDP complex were rapidly frozen under sterile condition, and lyophilized, to obtain CDDP complex lyophilized powder, wherein the conversion thereof was 85%.

The hydrodynamic radius of the micelle was measured, as shown in FIG. 1. FIG. 1 was a radius distribution diagram of the hydrodynamic radius of the CDDP complex prepared in Example 11 of the present disclosure. The results showed that the hydrodynamic radius of the CDDP complex micelles was 116 nm.

The obtained CDDP complex lyophilized powder was redissolved. The Pt content thereof was measured by inductance coupling plasma mass spectrum. The drug loading efficiency (DLE) and the drug loading content (DLC) were calculated according to the following formulae.

$$DLE = \frac{\text{the weight of } CDDP \text{ in the complex}}{\text{the weight of } CDDP \text{ added}} \times 100\%.$$

$$DLC = \frac{\text{the weight of } CDDP \text{ in the complex}}{\text{the weight of the complex}} \times 100\%.$$

Figure 5:
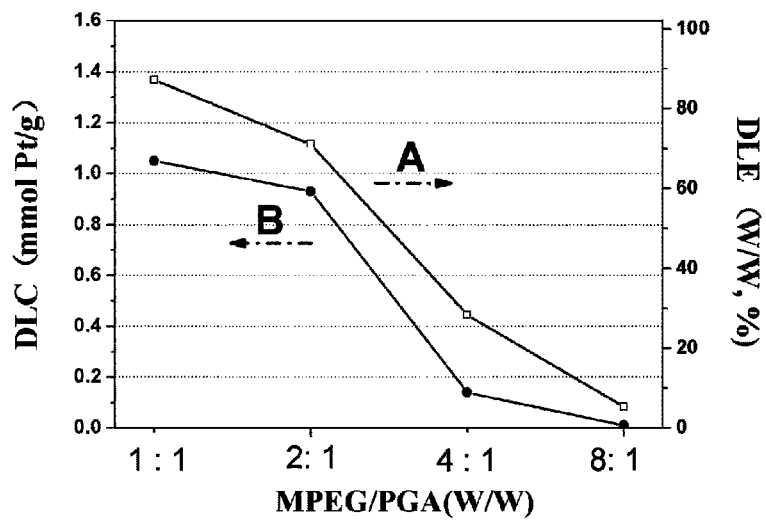
FIG. 5 is a changing trend diagram of the drug loading efficiency (DLE) and the drug loading content (DLC) of the CDDP complex prepared by Examples 11 to 14 of the present disclosure.

The results of the drug loading efficiency and the drug loading content of the CDDP complex obtained were shown in FIG. 5. FIG. 5 was a changing trend diagram of the drug loading efficiency and the drug loading content of the CDDP complex prepared by Examples 11 to 14 of the present disclosure, wherein curve A was the drug loading efficiency changing trend, curve B was the drug loading content changing trend. As seen from FIG. 5, the drug loading efficiency of CDDP complex prepared by Example 11 was 87.2%, and the drug loading content was 1.05 mmol Pt/g.

Example 12

55.3 mg of $P(Glu)_{160}$-g-$(mPEG_{45})_{20}$ prepared in Example 2 were dissolved in 25 mL of double distilled water. The pH value was adjusted to from 8 to 9. 18.7 mg of CDDP were added, and stirred under the condition of shielding light at 37° C. for 72 h. After removing free CDDP by dialysing with pure water for 24 h, during which time water was replaced for 6 times, micelles of the CDDP complex were obtained; the micelles of the CDDP complex were rapidly frozen under sterile condition, and lyophilized, to obtain CDDP complex lyophilized powder, wherein the conversion thereof was 80%.

Figure 2:
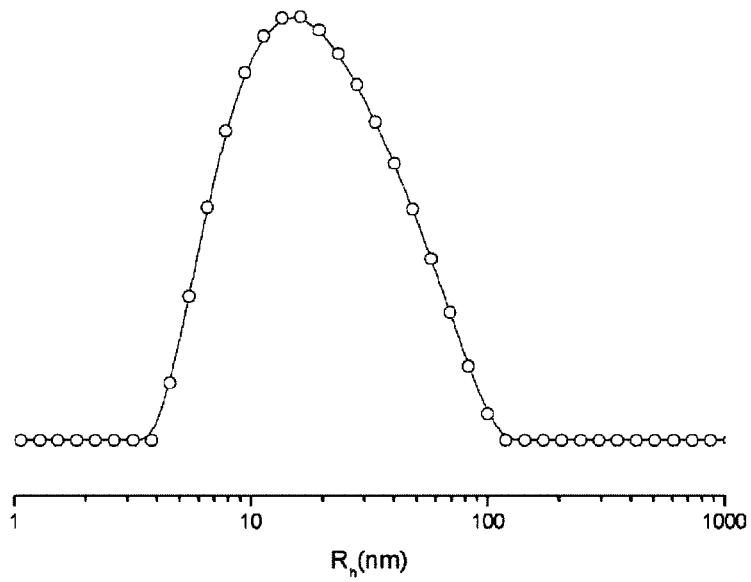
FIG. 2 is a radius distribution diagram of the hydrodynamic radius of the CDDP complex prepared in Example 12 of the present disclosure.

The hydrodynamic radius of the micelle was measured. The result was shown in FIG. 2. FIG. 2 was a radius distribution diagram of the hydrodynamic radius of the CDDP complex prepared in Example 12 of the present disclosure. The results showed that the hydrodynamic radius of the CDDP complex micelle was 23.9 nm.

The obtained CDDP complex lyophilized powder was redissolved. The Pt content thereof was measured by inductance coupling plasma mass spectrum. The drug loading efficiency (DLE) and the drug loading content (DLC) were calculated according to the following formulae;

$$DLE = \frac{\text{the weight of } CDDP \text{ in the complex}}{\text{the weight of } CDDP \text{ added}} \times 100\%.$$

$$DLC = \frac{\text{the weight of } CDDP \text{ in the complex}}{\text{the weight of the complex}} \times 100\%.$$

The results of the drug loading efficiency and the drug loading content of the CDDP complex obtained were shown in FIG. 5. FIG. 5 was a changing trend diagram of the drug loading efficiency and the drug loading content of the CDDP complex prepared by Examples 11 to 14 of the present disclosure, wherein curve A was the drug loading efficiency changing trend, curve B was the drug loading content changing trend. As seen from FIG. 5, the drug loading efficiency of CDDP complex prepared by Example 12 was 71.0%, and the drug loading content was 0.93 mmol Pt/g.

Example 13

110.3 mg of $P(Glu)_{160}$-g-$(mPEG_{45})_{40}$ prepared in Example 3 were dissolved in 25 mL of double distilled water. The pH value was adjusted to from 8 to 9. 18.7 mg of CDDP were added, and stirred under the condition of shielding light at 37° C. for 72 h. After removing free CDDP by dialysing with pure water for 24 h, during which time water was replaced for 6 times, micelles of the CDDP complex were obtained; the micelles of the CDDP complex were rapidly frozen under sterile condition, and lyophilized, to obtain CDDP complex lyophilized powder, wherein the conversion thereof was 76%.

Figure 3:
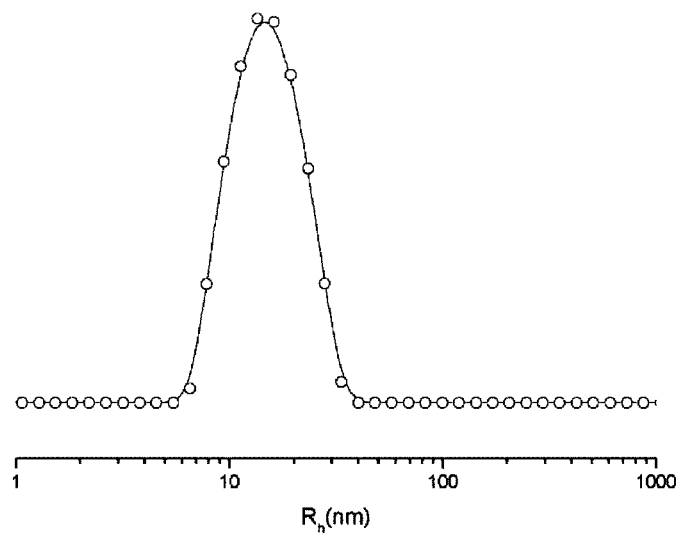
FIG. 3 is a radius distribution diagram of the hydrodynamic radius of the CDDP complex prepared in Example 13 of the present disclosure.

The hydrodynamic radius of the micelle was measured. The result was shown in FIG. 3. FIG. 3 was a radius distribution diagram of the hydrodynamic radius of the CDDP complex prepared in Example 13 of the present disclosure. The results showed that the hydrodynamic radius of the CDDP complex micelle was 15.7 nm.

The obtained CDDP complex lyophilized powder was redissolved. The Pt content thereof was measured by inductance coupling plasma mass spectrum. The drug loading efficiency (DLE) and the drug loading content (DLC) were calculated according to the following formulae;

$$DLE = \frac{\text{the weight of } CDDP \text{ in the complex}}{\text{the weight of } CDDP \text{ added}} \times 100\%.$$

$$DLC = \frac{\text{the weight of } CDDP \text{ in the complex}}{\text{the weight of the complex}} \times 100\%.$$

The results of the drug loading efficiency and the drug loading content of the CDDP complex obtained were shown in FIG. 5. FIG. 5 was a changing trend diagram of the drug loading efficiency and the drug loading content of the CDDP complex prepared by Examples 11 to 14 of the present disclosure, wherein curve A was the drug loading efficiency changing trend, curve B was the drug loading content changing trend. As seen from FIG. 5, the drug loading efficiency of CDDP complex prepared by Example 13 was 28.3%, and the drug loading content was 0.14 mmol Pt/g.

Example 14

300.0 mg of $P(Glu)_{160}$-g-$(mPEG_{45})_{80}$ prepared by Example 4 were dissolved in 25 mL of double distilled water. The pH value was adjusted to from 8 to 9. 18.7 mg of CDDP were added, and stirred under the condition of shielding light at 37° C. for 72 h. After removing free CDDP by dialysing with pure water for 24 h, during which time water was replaced for 6 times, micelles of the CDDP complex were obtained; the micelles of the CDDP complex were rapidly frozen under sterile condition, and lyophilized, to obtain CDDP complex lyophilized powder, wherein the conversion thereof was 75%.

Figure 4:
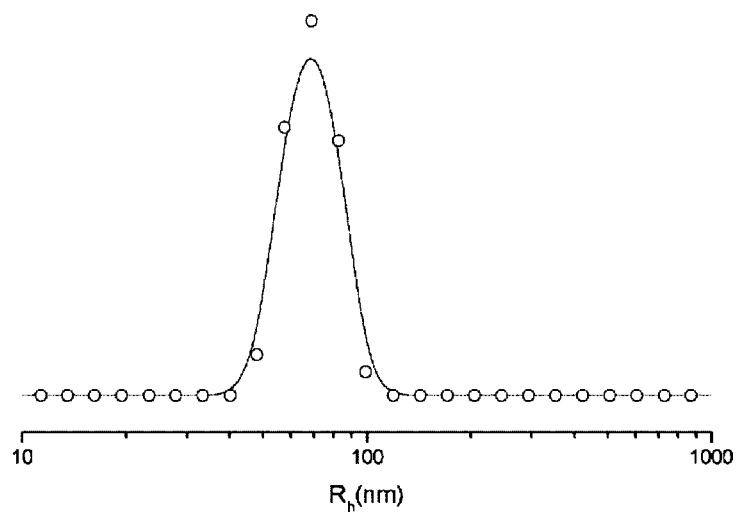
FIG. 4 is a radius distribution diagram of the hydrodynamic radius of the CDDP complex prepared in Example 14 of the present disclosure.

The hydrodynamic radius of the micelle was measured. The result was shown in FIG. 4. FIG. 4 was a radius distribution diagram of the hydrodynamic radius of the CDDP complex prepared in Example 14 of the present disclosure. The results showed that the hydrodynamic radius of the CDDP complex micelle was 69.3 nm.

The obtained CDDP complex lyophilized powder was redissolved. The Pt content thereof was measured by inductance coupling plasma mass spectrum. The drug loading efficiency (DLE) and the drug loading content (DLC) were calculated according to the following formulae;

$$DLE = \frac{\text{the weight of } CDDP \text{ in the complex}}{\text{the weight of } CDDP \text{ added}} \times 100\%.$$

$$DLC = \frac{\text{the weight of } CDDP \text{ in the complex}}{\text{the weight of the complex}} \times 100\%.$$

The results of the drug loading efficiency and the drug loading content of the CDDP complex obtained were shown in FIG. 5. FIG. 5 was a changing trend diagram of the drug loading efficiency and the drug loading content of the CDDP complex prepared by Examples 11 to 14 of the present disclosure, wherein curve A was the drug loading efficiency changing trend, curve B was the drug loading content changing trend. As seen from FIG. 5, the drug loading efficiency of CDDP complex prepared by Example 14 was 5.4%, and the drug loading content was 0.011 mmol Pt/g.

Example 15

50 mg of $P(Glu)_{160}$-g-$(mPEG_{45})_{10}$ prepared in Example 1 were subjected to a coordination reaction with different grains of CDDP, wherein the adding amounts were shown in Table 1. Table 1 indicated the adding amounts of $P(Glu)_{160}$-g-$(mPEG_{45})_{10}$ and CDDP. The loading amount and the drug loading efficiency of the CDDP complex obtained through calculation were shown in Table 2. Table 2 indicated the loading amount and the drug loading efficiency of the CDDP complex prepared in Example 15.

TABLE 1 the adding amounts of P(Glu)160-g-(mPEG45)$_{10}$ and CDDP

| No. | CDDP/mg | P(Glu)160-g-(mPEG45)$_{10}$/mg |
|---|---|---|
| 11 | 21.4 | 50 |
| 12 | 12.5 | 50 |
| 13 | 5.56 | 50 |

TABLE 2 the loading amount and drug loading efficiency of CDDP complex prepared in Example 15

| No. | loading amount (%) | drug loading efficiency (%) |
|---|---|---|
| 11 | 25.9% | 86.4% |
| 12 | 22.7% | 90.2% |
| 13 | 10.3% | 94.3% |

As seen from the results of Table 2, the CDDP complex had a high loading amount, and a good drug loading efficiency.

Example 16

50 mg of $P(Glu)_{160}$-g-$(mPEG_{45})_{20}$ prepared in Example 2 were subjected to a coordination reaction with different grains of CDDP, wherein the adding amounts were shown in Table 3. Table 3 indicated the adding amounts of $P(Glu)_{160}$-g-$(mPEG_{45})_{20}$ and CDDP. The loading amount and the drug loading efficiency of the CDDP complex obtained through calculation were shown in Table 4. Table 4 indicated the loading amount and the drug loading efficiency of the CDDP complex prepared in Example 16.

TABLE 3 the adding amounts of P(Glu)160-g-(mPEG45)$_{20}$ and CDDP

| No. | CDDP/mg | P(Glu)160-g-(mPEG45)$_{20}$/mg |
|---|---|---|
| 21 | 12.5 | 50 |
| 22 | 8.82 | 50 |
| 23 | 5.56 | 50 |

TABLE 4 the loading amount and drug loading efficiency of CDDP complex prepared in Example 16

| No. | loading amount (%) | drug loading efficiency (%) |
|---|---|---|
| 21 | 17.10% | 85.50% |
| 22 | 12.65% | 88.33% |
| 23 | 10.09% | 95.36% |

As seen from the results of Table 4, the CDDP complex had a high loading amount, and a good loading efficiency.

Example 17

Figure 6:
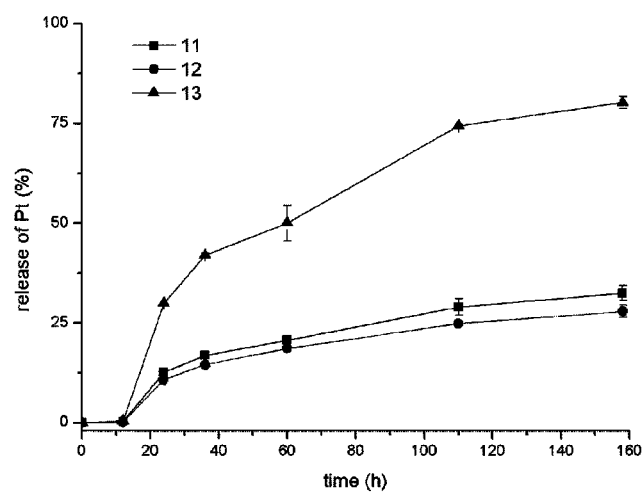
FIG. 6 is a plotted curve of the release of CDDP from the CDDP complexes prepared in Examples 17 to 19 of the present disclosure at pH=7.4.

Under the condition of 37° C., 5 mg of CDDP complex 11 prepared in Example 15 were weighted, dissolved in 5 mL of 0.01M phosphate buffer solution having a pH value of 7.4, and then transferred into a dialysis bag with a retention molecular weight of 3500. 40 mL of a buffer solution having corresponding pH value were used in the dialysis. 3 mL of samples were taken at 12 h, 24 h, 36 h, 60 h, 108 h and 156 h, respectively, and corresponding amount of buffer solution were added. Quantitative analysis was conducted using inductance coupling plasma mass spectrum, to obtain the change of the accumulated releasing percent along with the increase of the time. The releasing result was shown by FIG. 6. FIG. 6 was a plotted curve of the release of CDDP from the CDDP complexes prepared in Examples 17 to 19 of the present disclosure at pH=7.4. As seen from FIG. 6, the CDDP complex had a sustained release capability.

Example 18

Under the condition of 37° C., Sing of CDDP complex 12 prepared in Example 15 were weighted, dissolved in 5 mL of 0.01M phosphate buffer solution having a pH value of 7.4, and then transferred into a dialysis bag with a retention molecular weight of 3500. 40 mL of a buffer solution having corresponding pH value were used in the dialysis. 3 mL of samples were taken at 12 h, 24 h, 36 h, 60 h, 108 h and 156 h, respectively, and corresponding amount of buffer solution were added. Quantitative analysis was conducted using inductance coupling plasma mass spectrum, to obtain the change of the accumulated releasing percent along with the increase of the time. The releasing result was shown by FIG. 6. FIG. 6 was a plotted curve of the release of CDDP from the CDDP complexes prepared in Examples 17 to 19 of the present disclosure at pH=7.4. As seen from FIG. 6, the CDDP complex had a sustained release capability.

Example 19

Under the condition of 37° C., Sing of CDDP complex 13 prepared in Example 15 were weighted, dissolved in 5 mL of 0.01M phosphate buffer solution having a pH value of 7.4, and then transferred into a dialysis bag with a retention molecular weight of 3500. 40 mL of a buffer solution having corresponding pH value were used in the dialysis. 3 mL of samples were taken at 12 h, 24 h, 36 h, 60 h, 108 h and 156 h, respectively, and corresponding amount of buffer solution were added. Quantitative analysis was conducted using inductance coupling plasma mass spectrum, to obtain the change of the accumulated releasing percent along with the increase of the time. The releasing result was shown by FIG. 6. FIG. 6 was a plotted curve of the release of CDDP from the CDDP complexes prepared in Examples 17 to 19 of the present disclosure at pH=7.4. As seen from FIG. 6, the CDDP complex had a sustained release capability.

Example 20

Figure 7:
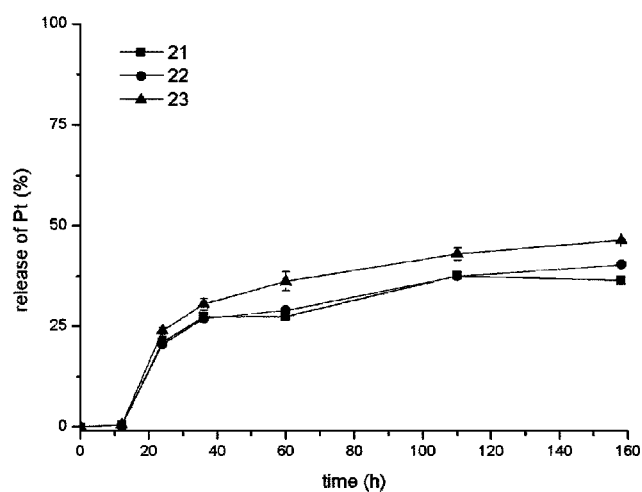
FIG. 7 is a plotted curve of the release of CDDP from the CDDP complexes prepared in Examples 20 to 22 of the present disclosure at pH=7.4.

Under the condition of 37° C., 5 mg of CDDP complex 21 prepared in Example 16 were weighted, dissolved in 5 mL of 0.01M phosphate buffer solution having a pH value of 7.4, and then transferred into a dialysis bag with a retention molecular weight of 3500. 40 mL of a buffer solution having corresponding pH value were used in the dialysis. 3 mL of samples were taken at 12 h, 24 h, 36 h, 60 h, 108 h and 156 h, respectively, and corresponding amount of buffer solution were added. Quantitative analysis was conducted using inductance coupling plasma mass spectrum, to obtain the change of the accumulated releasing percent along with the increase of the time. The releasing result was shown by FIG. 7. FIG. 7 was a plotted curve of the release of CDDP from the CDDP complexes prepared in Examples 20 to 22 of the present disclosure at pH=7.4. As seen from FIG. 7, the CDDP complex had a sustained release capability.

Example 21

Under the condition of 37° C., Sing of CDDP complex 22 prepared in Example 16 were weighted, dissolved in 5 mL of 0.01M phosphate buffer solution having a pH value of 7.4, and then transferred into a dialysis bag with a retention molecular weight of 3500. 40 mL of a buffer solution having corresponding pH value were used in the dialysis. 3 mL of samples were taken at 12 h, 24 h, 36 h, 60 h, 108 h and 156 h, respectively, and corresponding amount of buffer solution were added. Quantitative analysis was conducted using inductance coupling plasma mass spectrum, to obtain the change of the accumulated releasing percent along with the increase of the time. The releasing result was shown by FIG. 7. FIG. 7 was a plotted curve of the release of CDDP from the CDDP complexes prepared in Examples 20 to 22 of the present disclosure at pH=7.4. As seen from FIG. 7, the CDDP complex had a sustained release capability.

Example 22

Under the condition of 37° C., Sing of CDDP complex 23 prepared in Example 16 were weighted, dissolved in 5 mL of 0.01M phosphate buffer solution having a pH value of 7.4, and then transferred into a dialysis bag with a retention molecular weight of 3500. 40 mL of a buffer solution having corresponding pH value were used in the dialysis. 3 mL of samples were taken at 12 h, 24 h, 36 h, 60 h, 108 h and 156 h, respectively, and corresponding amount of buffer solution were added. Quantitative analysis was conducted using inductance coupling plasma mass spectrum, to obtain the change of the accumulated releasing percent along with the increase of the time. The releasing result was shown by FIG. 7. FIG. 7 was a plotted curve of the release of CDDP from the CDDP complexes prepared in Examples 20 to 22 of the present disclosure at pH=7.4. As seen from FIG. 7, the CDDP complex had a sustained release capability.

Example 23

A549 cells in log phase were collected, adjusted the cell concentration, and seeded into a 96-well plate. Each well had 100 μL (about $10^4$) of cells. Culture solution was discarded after incubating at 37° C. for 24 h.

The free drug of CDDP was diluted with the culture medium into 6 samples having concentrations of 40 µg/mL, 20 µg/mL, 10 µg/mL, 5 µg/mL, 2.5 µg/mL, and 1.25 µg/mL, respectively. Each of three CDDP complexes (11, 12, 13) prepared in Example 15 was diluted with the culture medium into 6 samples having concentrations of 40 µg/mL, 20 µg/mL, 10 µg/mL, 5 µg/mL, 2.5 µg/mL, and 1.25 µg/mL in terms of Pt concentration in the CDDP.

Figure 8:
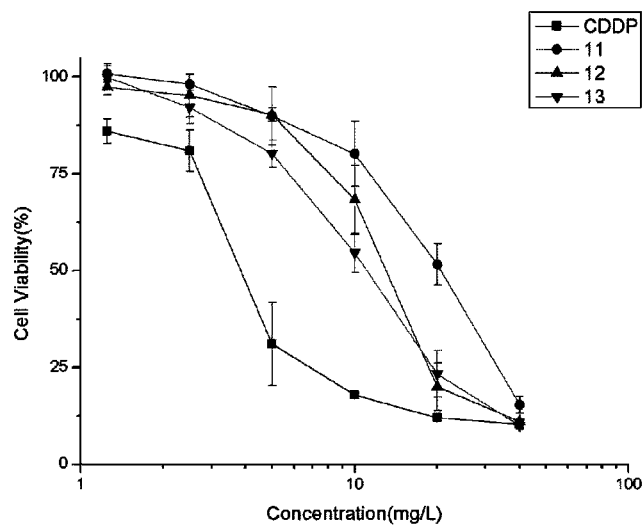
FIG. 8 is a diagram showing the drug efficiency test results of three CDDP complexes prepared in Example 15 of the present disclosure and free drug of CDDP for A549 cells.

Each sample was added into the 96-well plate, with 200 µL added into each well, and each concentration added into 6 wells, and was incubated in a cell incubator at 37° C., under saturated humidity and 5% $CO_2$ for 24 h. After 24 h, 20 µL of thiazole blue in a concentration of 5 mg/mL were added into each well. The incubation was continued for 4 h and then stopped. Culture solution in wells was drawn out. Into each well, 150 µL of dimethyl sulfoxide were added, and shaken at a low speed for 10 min. The adsorption of each well at 492 nm was measured using an enzyme-labeled instrument, and the cell viability after the use of the free drug of CDDP and the CDDP complex at each concentration was obtained by calculation. The result was shown in FIG. 8. FIG. 8 was a drug effect test result diagram of three CDDP complexes prepared in Example 15 of the present disclosure and the free drug of CDDP for A549 cell. As seen from FIG. 8, comparing with the free drug of CDDP, the CDDP complex had a substantive sustained release function, meanwhile, it also showed an obvious dosage-effect relationship.

Example 24

A549 cells in log phase were collected, adjusted the cell concentration, and seeded into a 96-well plate. Each well had 100 µL (about $10^4$) of cells. Culture solution was discarded after incubating at 37° C. for 24 h.

The free drug of CDDP was diluted with the culture medium into 6 samples having concentrations of 40 µg/mL, 20 µg/mL, 10 µg/mL, 5 µg/mL, 2.5 µg/mL, and 1.25 µg/mL, respectively. Each of three CDDP complexes (21, 22, 23) prepared in Example 16 was diluted with the culture medium into 6 samples having concentrations of 40 µg/mL, 20 µg/mL, 10 µg/mL, 5 µg/mL, 2.5 µg/mL, and 1.25 µg/mL in terms of Pt concentration in the CDDP.

Figure 9:
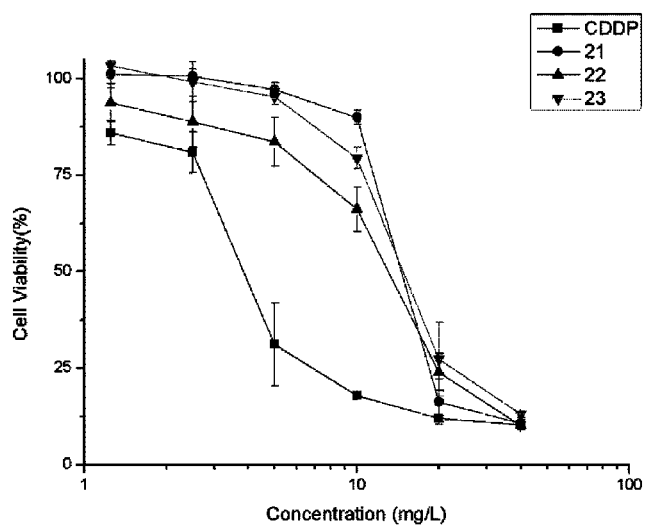
FIG. 9 is a diagram showing the drug efficiency test results of three CDDP complexes prepared in Example 16 of the present disclosure and free drug of CDDP for A549 cells.

Each sample was added into the 96-well plate, with 200 µL added into each well, and each concentration added into 6 wells, and was incubated in a cell incubator at 37° C., under saturated humidity and 5% $CO_2$ for 24 h. After 24 h, 20 µL of thiazole blue in a concentration of 5 mg/mL were added into each well. The incubation was continued for 4 h and then stopped. Culture solution in wells was drawn out. Into each well, 150 µL of dimethyl sulfoxide were added, and shaken at a low speed for 10 min. The adsorption of each well at 492 nm was measured using an enzyme-labeled instrument, and the cell viability after the use of the free drug of CDDP and the CDDP complex at each concentration was obtained by calculation. The result was shown in FIG. 9. FIG. 9 was a drug effect test result diagram of three CDDP complexes prepared in Example 16 of the present disclosure and the free drug of CDDP for A549 cell. As seen from FIG. 9, comparing with the free drug of CDDP, the CDDP complex had a substantive sustained release function, meanwhile, it also showed an obvious dosage-effect relationship.

The above described embodiments are only preferred ones of the present disclosure. It should be pointed out that, for a skilled person in the art, various modifications and amendments can be made without departing from the principle of the present disclosure. These modifications and amendments should be deemed as a part of the protection scope of the present disclosure.

What is claimed is:

1. A cis-diamminedichloroplatinum (CDDP) complex, which is formed by complexation of CDDP and a polymer having a structure of Formula (I),

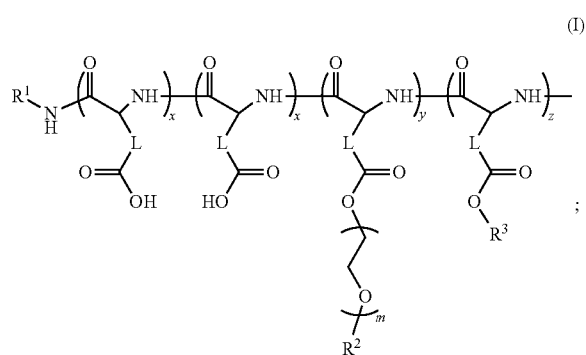

in formula (I), $R^1$ is independently selected from a C2 to C10 linear alkyl group, a C3 to C10 branched alkyl group, a phenyl group or a group of R'—CO—, where R' is independently selected from a C2 to C10 linear alkyl group, a C3 to C10 branched alkyl group or a phenyl group;

$R^2$ is independently selected from a hydrogen atom, a C1 to C20 alkyl group or a substituted C1 to C20 alkyl group, where the substituent for the substituted alkyl group is one or more selected from a ketal, an acetal, a hydroxyl group, an aldehyde group, an amino group, a mercapto group, and a glycosyl residue;

$R^3$ is independently selected from a hydrogen atom or a cation;

L is independently selected from —$CH_2$— or —$CH_2$—$CH_2$—;

m is a polymerization degree, where $40 \leq m \leq 250$; and x, y, and z are polymerization degrees, where $10 \leq 2x+y+z \leq 5000$, $5\% \leq y/(2x+y+z) \leq 80\%$.

2. The CDDP complex according to claim 1, wherein, $R^2$ is independently selected from a hydrogen atom, a C1 to C10 alkyl group or a substituted C1 to C10 alkyl group; and $R^3$ is independently selected from a hydrogen atom, a metal cation or an organic cation.

3. The CDDP complex according to claim 2, wherein, $R^3$ is independently selected from a hydrogen atom, a sodium ion, a potassium ion, a magnesium ion, an ammonium ion or an amino acid ion.

4. The CDDP complex according to claim 1, wherein, $30 \leq 2x+y+z \leq 300$, and $5\% \leq y/(2x+y+z) \leq 50\%$.

5. The CDDP complex according to claim 1, wherein, $R^1$ is a C6 alkyl group, $R^2$ is a methyl group, $R^3$ is a hydrogen atom or a sodium ion, and L is —$CH_2$—$CH_2$—.

6. A method of preparing a cisplatin CDDP complex, comprising subjecting CDDP to a coordination reaction with a polymer having a structure of Formula (I) in an aqueous medium,

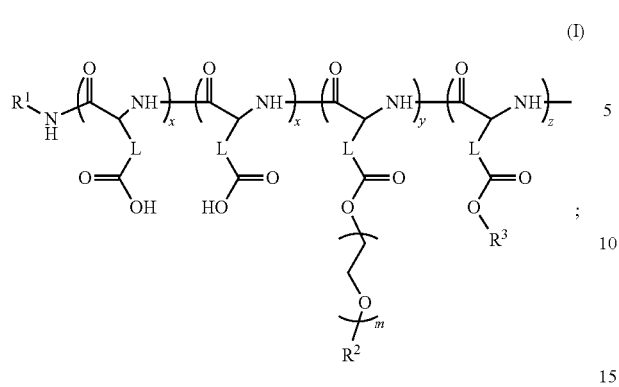

(I)

wherein:
in formula (I), $R^1$ is independently selected from a C2 to C10 linear alkyl group, a C3 to C10 branched alkyl group, a phenyl group or a group of R'—CO—, where R' is independently selected from a C2 to C10 linear alkyl group, a C3 to C10 branched alkyl group or a phenyl group;

$R^2$ is independently selected from a hydrogen atom, a C1 to C20 alkyl group or a substituted C1 to C20 alkyl group, where the substituent for the substituted alkyl group is one or more selected from a ketal, an acetal, a hydroxyl group, an aldehyde group, an amino group, a mercapto group, and a glycosyl residue;

$R^3$ is independently selected from a hydrogen atom or a cation;

L is independently selected from —CH$_2$— or —CH$_2$—CH$_2$—;

m is a polymerization degree, where $40 \leq m \leq 250$; and x, y, and z are polymerization degrees, where $10 \leq 2x+y+z \leq 5000$, $5\% \leq y/(2x+y+z) \leq 80\%$.

7. The method according to claim 6, wherein, the molar ratio between the carboxyl group of the polymer having a structure of Formula (I) and platinum (Pt) in the CDDP is less than 10.

8. The method according to claim 6, wherein the aqueous medium is water, physiological saline, a buffer solution, a tissue culture solution, or a body fluid.

9. The method according to claim 6, wherein the method further comprises:
subjecting a polymer having a structure of Formula (II) and a polymer having a structure of Formula (III) to a graft reaction in the presence of both a dehydrating agent and a catalyst, to obtain the polymer having a structure of Formula (I);

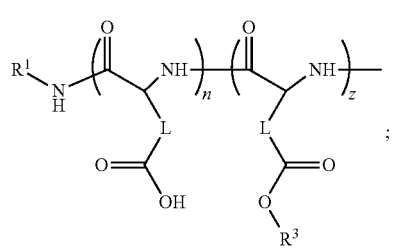

(II)

(III)

in Formula (II), $R^1$ is independently selected from a C2 to C10 linear alkyl group, a C3 to C10 branched alkyl group, a phenyl group or a group of R'—CO—, where R' is independently selected from a C2 to C10 linear alkyl group, a C3 to C10 branched alkyl group or a phenyl group;

$R^3$ is independently selected from a hydrogen atom or a cation;

L is independently selected from —CH$_2$— or —CH$_2$—CH$_2$—; and each of n, z is a polymerization degree, where $10 \leq n+z \leq 5000$;

in Formula (III), $R^2$ is independently selected from a hydrogen atom, a C1 to C20 alkyl group or a substituted C1 to C20 alkyl group; and m is a polymerization degree, where $40 \leq m \leq 250$.

10. The method according to claim 9, wherein, the dehydrating agent is one or more selected from the group consisting of 1-(3-dimethyl aminopropyl)-3-ethylcarbodiimide hydrochloride, N,N-diisopropyl carbodiimide, and N,N'-dicyclohexyl carbodiimide.

* * * * *

UNITED STATES PATENT AND TRADEMARK OFFICE
CERTIFICATE OF CORRECTION

PATENT NO. : 9,629,923 B2
APPLICATION NO. : 14/434731
DATED : April 25, 2017
INVENTOR(S) : Tang et al.

It is certified that error appears in the above-identified patent and that said Letters Patent is hereby corrected as shown below:

On the Title Page

Item (72), (Inventors) at Lines 4-5, change "Xiuli Zuang," to --Xiuli Zhuang,--.

In the Specification

In Column 1 at Line 67, change "lose" to --loss--.

In Column 23 at Line 35, change "Sing" to --5 mg--.

In Column 23 at Line 54, change "Sing" to --5 mg--.

In Column 24 at Line 26, change "Sing" to --5 mg--.

In Column 24 at Line 45, change "Sing" to --5 mg--.

Signed and Sealed this
Tenth Day of April, 2018

Andrei Iancu
*Director of the United States Patent and Trademark Office*